(12) United States Patent
Shadduck

(10) Patent No.: US 6,319,274 B1
(45) Date of Patent: Nov. 20, 2001

(54) DEVICES AND TECHNIQUES FOR LIGHT-MEDIATED STIMULATION OF TRABECULAR MESHWORK IN GLAUCOMA THERAPY

(76) Inventor: John H. Shadduck, 1490 Vistazo West St., Tiburon, CA (US) 94920

( * ) Notice: Subject to any disclaimer, the term of this patent is extended or adjusted under 35 U.S.C. 154(b) by 0 days.

(21) Appl. No.: 09/102,533

(22) Filed: Jun. 22, 1998

(51) Int. Cl.[7] .................................................... A61M 5/06
(52) U.S. Cl. ................................. 607/89; 607/88; 607/90; 606/3; 606/13
(58) Field of Search .............................. 606/2, 3, 10–13; 607/88–96

(56) References Cited

U.S. PATENT DOCUMENTS 5,259,380 * 11/1993 Mendes et al. ............................ 606/3
5,372,595 * 12/1994 Gaasterland et al. ................... 606/13

* cited by examiner

*Primary Examiner*—David M. Shay

(57) ABSTRACT

An apparatus and technique for transscleral light-mediated biostimulation of the trabecular plates of a patient's eye in a treatment for glaucoma or ocular hypertension. The apparatus includes; (i) a working end geometry for contacting the anterior surface of the sclera and cornea to insure that a laser emission reaches the trabecular meshwork from a particular location on the anterior surface of the sclera, (ii) a laser energy source providing a wavelength appropriate for absorption beneath the anterior scleral surface to the depth of the trabecular plates, and (iii) a dosimetry control system for controlling the exposure of the laser emission at the particular spatial locations. The device uses a light energy source that emits wavelengths in the near-infrared portion of the spectrum, preferably in the range of about 1.30 $\mu$m to 1.40 $\mu$m or from about 1.55 $\mu$m to 1.85 $\mu$m. The depth of absorption of such wavelength ranges will extend through most, if not all, of the thickness of the sclera (750 $\mu$m to 950 $\mu$m). In accordance with a proposed method of trabecular biostimulation, the targeted region is elevated in temperature to a range between about 40° C. to 55° C. for a period of time ranging from about 1 second to 120 seconds or more.

10 Claims, 18 Drawing Sheets

| temperature (C°) | 35 | 42 | 60 | 70 | 100 | 450 | 600 |
|---|---|---|---|---|---|---|---|
| | CORE BODY TEMP. | | COLLAGEN SHRINKAGE RANGE | COAGULATION DENATURATION RANGE | THRESHOLD FOR VAPORIZATION OF CELL CONTENTS | THRESHOLD FOR THERMAL CUTTING OF TISSUE | THRESHOLD FOR PYROLYSIS OF TISSUE |
| effects in tissue | none | | tissue contraction | cell death hemostasis thermal damage | tissue cutting minimal to moderate thermal damage | tissue cutting minimal to moderate thermal damage | tissue ablation significant thermal damage |
| methods to produce effects in tissue | | | conduction, convection from heated media  de-focused laser beam  electrical current flow  microwave  ultrasound | conduction, convection from heated media  laser beam  electrical current flow  microwave | arc from electrosurgical electrode | conduction from heated surface  conduction from laser-heated fiber tip | intense arc from electrosurgical electrode  high energy density laser beam |

Photoexcitation modality: 35–60
Photocoagulation modality: 60–100
Photodisruption modality: 100–600

FIG. 4B

DEVICES AND TECHNIQUES FOR LIGHT-MEDIATED STIMULATION OF TRABECULAR MESHWORK IN GLAUCOMA THERAPY

BACKGROUND OF THE INVENTION

1. Field of the Invention

The present invention relates to the field of medical therapeutics and more specifically relates to the field of glaucoma and ocular hypertension therapy utilizing novel instruments and techniques for opto-thermal mediation of a patient's trabecular meshwork for enhancing the mitotic rate of endothelial meshwork cells and for reduction of biostructural laxity within the meshwork, which meshwork biocharacteristics may be subject to cell-division inhibitions and/or other degradations.

2. Description of the Related Art

Glaucomas comprise a group of debilitating eye diseases that are the leading cause of blindness in the United States and around the world. The pathophysiological mechanisms of glaucomas are not fully understood. The principal sign of the disease is elevated intraocular pressure (IOP). Such elevations of IOP ultimately can cause damage to the optic nerve head and result in impairment to, or loss of, normal visual function. It is known that elevated IOP is caused by an excess of fluid or aqueous AQ within the eye, which is continually produced by the ciliary body CB and drained through the trabecular meshwork M to leave the eye or globe 5 (see FIGS. 1A–1D). The excess intraocular fluid generally results from blockage or impairment of the normal drainage from the anterior chamber AC via the trabecular meshwork M. The meshwork consists of about 10 to 25 layers of perforated trabecular plates ($TP_1 \ldots TP_r$) or sheets around the filtration angle FA of the anterior chamber AC, having a width of about 1,000 μm to 1,500 μm (1.0 mm. to 1.5 mm.) in a circumference ranging from 35,000 to 40,000 μm. FIGS. 1A–1B show electron micrographs of trabecular plates TP with FIG. 1B including a representation of an endothelial cell layer EC of trabecular beam B with the beam core BC believed to be predominantly collagen and GAGs (glucosaminoglycans) or ground substance. FIG. 1C illustrates that each successively deeper plate (more anterior plate) of the meshwork M has smaller perforations PF or openings between the beams B than more exposed (posterior) trabecular plates. Further, the intraplate spacing IPS diminishes with the successively deeper plates (FIG. 1C). The meshwork M thus serves as a filtration mechanism wherein cellular detritus, etc. in the aqueous outflow is captured before it passes into Schlemm's canal SCH where the aqueous is transported away form the eye (FIG. 1D). The meshwork M lies about 750 μm to 950 μm beneath the anterior surface of the sclera SC.

A number of ophthalmic disease conditions are related to the trabecular meshwork and can be linked to distinct processes or pathological conditions within a patient's eye. Any disease of the trabecular meshwork shares the characteristic of elevating IOP. Chandler et al. described many forms of glaucoma, the principal ones being: primary open-angle glaucoma (POAG); progressive low-tension glaucoma; pigment dispersion and pigmentary glaucoma; angle-closure glaucoma; combined open-angle and angle-closure glaucoma, exfoliation and open-angle glaucoma; angle-closure glaucoma due to multiple system cysts of iris and ciliary body; angle-closure glaucoma secondary to occlusion of the central retina vein; angle-closure glaucoma secondary to bilateral transitory myopia; ghost-cell glaucoma; lens-induced glaucoma; glaucoma due to intraocular inflammation; neovascular glaucoma; glaucoma associated with extraocular venous congestion; essential atrophy of the iris with glaucoma. among others. (Chandler, et. al., *Glaucoma*, 3rd Ed., Lea & Febliger; Phila. (1986)) In all of the above-listed glaucoma syndromes, elevated IOP results from an increase in resistance to aqueous humor outflows through the trabecular meshwork.

In terms of incidence, primary open-angle glaucoma (POAG) is the most prevalent form of the disease affecting up to 0.5% of the population between ages of 35 to 75. The incidence of glaucoma rises with age to over 6% of the population 75 years are older. One identifiable component of the POAG syndrome is the loss of endothelial cells within the meshwork which is associated with a degeneration of the normal trabecular biostructure. It is known that the human aging process itself leads to a progressive loss of trabecular endothelial cells EC which compromises normal aqueous outflows therethrough. When examined in tissue cultures, degraded endothelial tissue from POAG patients appears similar to that of "aging" individuals.

Other characteristics believed common to POAG (as well as many other glaucomas listed above) relate to a biostructural obstructive syndrome of the trabecular plates TP, for example, resulting from compression of the plates into a matt-like form that reduces intraplate spacing IPS (FIG. 1C). This factor reduces the capacity of the meshwork to act as a filtering mechanism and may develop after the meshwork is clogged with cellular detritus, pigments, etc. Such an obstructive syndrome, it is believed, also is characterized by increased laxity of the trabecular beams B allowing their collapse which thus reduces intraplate spacing. The most likely causes of the meshwork degradations described above may be cumulative stresses from various factors (e.g., oxidative, phagocytic, glucocorticoidal stresses). The fact that increased outflow resistance appears in the non-glaucoma "aging" population further suggests that both trabecular endothelial cellular processes and an obstructive meshwork syndrome play significant roles in decreasing aqueous outflows.

The normal IOP for humans usually ranges from about 10 to 22 mm. Hg. (1.3–2.7 kilopascals) and is maintained by a balance in the aqueous production by the ciliary body CB, inflows to the anterior chamber AC and outflows therefrom. As described above, in a normal eye, the aqueous drains from the anterior chamber through the meshwork into Schlemm's canal SCH, through which it leaves the eye. In patients in a glaucomous state, besides passing through Schlemm's canal, the aqueous may also pass through the ciliary muscle CM into the suprachoroidal space and finally leave the eye through the sclera SC (FIG. 1D).

For purposes of description, the intraocular pressure (IOP) in a human can be defined by a formula of the following type:

$$IOP = P_e + (F_t - F_{uv}) \times R : (TM_{cep}, TM_{sp}, TM_{br})$$

where $P_e$ is the episcleral venous pressure (generally regarded as being around 9 mm. Hg.); $F_t$ is the total outflow of the aqueous humor from the anterior chamber, $F_{uv}$ is the fraction of aqueous passing by the uveoscleral route; R is the resistance to outflow of aqueous through the trabecular meshwork into Schlemm's canal, which can be considered to be functionally related to (i) the vitality of trabecular endothelial cellular cellular and enzymatic processes ($TM_{cep}$), (ii) the dimensions of intraplate spacing between ($TM_{ips}$) relative to a norm, and (iii) the trabecular beam resiliency ($T_{br}$) or biostructural tension within the meshwork under the pressure of aqueous outflow therethrough. Such a formula is useful for understanding the targets of various prior art therapies, if not for use as an actual mathematical model.

Among several therapies targeted at various elements of the above equation, two forms of treatment are common: (i) medical or drug therapies, and (ii) trans-corneal laser irradiation of the trabecular meshwork via a goniolens (see FIG. 2A). In medication therapies, the objective may be to lower IOP by either of several routes: reducing the aqueous flow total ($F_t$ in the above equation); increasing uveoscieral flow ($F_{uv}$ in above equation); or altering resistance to outflow (R), by stimulating endothelial cellular processes ($TM_{cep}$) which is believed to act on outflow resistance. Drug therapies have the disadvantages of requiring a lifelong treatment; causing significant side effects; being very costly (between $1,000–$2,000/yr.); and being unavailable or unaffordable in lesser developed countries of the world where the incidence of glaucoma is highest.

In the laser therapies, ALT (argon laser trabeculoplasty) and SLT (selective laser trabeculoplasty) have been developed which both rely on a trans-corneal approach to the posterior surface of the meshwork. Introduced in the 1980's, ALT uses an argon laser operating at a wavelength ($\lambda$) of 488 nm to 514.5 nm with a long pulse duration of about 0.10 second and a power range of from 500–1000 mW to irradiate a series of about 50 spots only around the 180° of the meshwork (see FIG. 2A). In ALT, the ophthalmologist utilizes a goniolens to direct laser beam strikes on the exposed surface of the trabecular plates TP. The causative mechanisms of ALT have never been clearly understood. It has been proposed that each ALT beam's incidence on the meshwork causes a burn or a melt and results in the formation of scar tissue that contracts (or tensions) a portion of the meshwork around the burn (cf. $TM_{br}$ or resiliency of beam B in above formula). According to another view, the ALT meshwork burns cause a wound healing response resulting in significant cell division and the transient repopulation of endothelial meshwork cells, at least in zones around the burns (cf. $TM_{cep}$ above). FIG. 2B shows an electron micrograph of an ALT meshwork burn indicated at 6, which may tension the meshwork at the burn periphery indicated at 7. A principal disadvantage of ALT is that it can only be performed twice on an eye—once in the superior (or nasal) 180 degrees of the meshwork and once in the inferior (or temporal) 180 degrees. The laser melts are too significant to repeat the treatment in the same portion of the meshwork.

The more recently developed trans-corneal laser approach is SLT, which uses a short-pulse, frequency-doubled, 530 nm Nd:YAG laser with pulse duration of 3 nanoseconds and energy levels that range from 0.60 mJ to 1.20 mJ. The SLT modality is called "selective photothermolysis" by its inventor (Dr. M. Latina) wherein the proposed wavelength is absorbed by endogenous pigment within the meshwork which kills (or lyses) the pigmented cells without damaging the non-pigmented cells (see U.S. Pat. No. 5,549,596). In theory, the short pulses allow heat to dissipate from the absorbing pigmented cells before killing adjacent cells (see FIG. 3). The SLT inventor proposes that the causative mechanisms of increasing aqueous outflows relate to (i) an inflammatory response in the meshwork that results in activation of enzyme systems that clean up the meshwork, and (ii) a mild expansion of the meshwork plates or perforations by killing pigmented cells with a photothermal or microcavitation effect (FIG. 3). The following table compares the ALT and SLT parameters.

|  | $\lambda$ | Pulse Duration | Power | Beam Size | Treatment Area |
|---|---|---|---|---|---|
| ALT | 488–514.5 nm | 0.1 second | 500–1000 mW | 50 $\mu$m | 50 spots/ 180° |
| SLT | 530 nm | 3 nanoseconds | 0.6–1.2 mJ | 300–400 $\mu$m | 50 spots/ 180° |

Several disadvantages are associated with the ALT/SLT modalities. First, both systems approach the meshwork through the anterior chamber AC by means of a goniolens. For this reason, the wavelengths must be selected from a portion of the spectrum that penetrates through the cornea C and aqueous AQ without the light energy being absorbed and extinguished—a distance of about 4 mm. to 8 mm. (4000 $\mu$m to 8000 $\mu$m). This factor greatly limits the choice of possible wavelengths—each of which has a different absorption coefficient in water (see FIG. 4A). The requirement of using a goniolens along with a laser aiming beam also makes the ALT/SLT approach technique dependent—making the therapy available only to highly skilled surgeons.

A second disadvantage the ALT/SLT modalities relates to the lack of exact understandings of the causative mechanisms for improving outflow facility. Since ALT has effects that last for about 5 years at most—and can be repeated only once—the medical and surgical communities have not developed a consensus about sequencing medical and surgical therapies. Glaucoma is a disease state that requires lifelong management. Some physicians propose that ALT be resorted to only after drug therapies have lost their effectiveness; other physicians propose ALT as a first line of defense in order to delay a lifetime of drug therapy and the attendant side effects.

Other significant disadvantages of ALT/SLT relate to the fact that both deliver similar photothermal effects to a limited depth within the trabecular plate structure. That is, the ALT/SLT causative mechanisms—no matter what they are—probably only operate within the trabecular plates TP most exposed to the incident beam which thus absorb the beam's photonic energy. This factor suggests that only the first few plates (most posterior plates) exposed to the anterior chamber AC are affected by such energy delivery—perhaps only about 10%–20% of the larger dimensioned trabecular plates. It is postulated that the underlying (anterior) trabecular plates that have smallest dimensioned perforations PF and the least intraplate spacing IPS are degraded to the greatest degree and thus play the most significant role in increasing IOP by clogging the pathways to Schlemm's canal (see FIG. 1D). Yet, these most anterior meshwork regions probably remain untreated by ALT and SLT.

Further, studies have shown that ALT is not effective in all patients, and actually increases IOP in over 20% of patients. Additionally, in recent SLT patients, the following complications have been documented: uveitis in the form of iritis in virtually all treated eyes; corneal burns in up to 25% of treated eyes; and anterior synechiae or adhesions due to the significant absorption of light energy in the pigmented cells of the meshwork.

What is needed is an improved technique for effecting biostructural changes in the trabecular meshwork to facilitate aqueous outflows that provides: (i) means for stimulating endothelial cell division to cause cell repopulation and rejuvenation within the trabecular plate structure; (ii) means for inducing a slight inflammatory or wound healing response to activate enzymatic systems such as stromolysin and metalloproteases that may help clean up the meshwork; (iii) means for causing the desired biostimulative effects without photocoagulation, photodisruption or photothermolysis of endothelial layers of the meshwork as in ALT/SLT; (iv) MIS (minimally invasive surgical) means for causing the desired effects in a repeatable maintenance therapy that can continue over the lifetime of the glaucoma patient; (v) MIS means for meshwork treatment that can be evaluated in all patients before resorting to drug therapies; (vi) MIS means for treating 360° of the meshwork instead of 180° or less; (vii) means for causing the desired effects substantially equally on all trabecular plates from the most posterior to the most anterior; (viii) MIS means simultaneous treatment of a substantial arc of the meshwork with a device in a single treatment position rather than time-consuming treatment in a series of spots; (ix) MIS means for biostimulating the trabecular structure in the many forms of glaucoma (other than POAG) that are not possible with a goniolens and laser strikes through the anterior chamber, (x) MIS means for treating the meshwork without risk of any corneal burns; and (xi) MIS means for treating the trabecular structure that is not technique-dependent and capable of being performed by optometrists or other lesser-skilled health care professionals in the lesser developed countries of the world.

SUMMARY OF THE INVENTION

The laser system and handpiece of the present invention are particularly adapted for use in elevating the temperature of a patient's trabecular meshwork for purposes of stimulating cellular processes. The system is adapted for a novel transscleral approach (instead of trans-corneal) and is called opto-thermal transscleral trabeculoplasty (or $OT^3$). The present invention provides cooperating means to develop biostimulative opto-thermal effects in a patient's trabecular meshwork, including a working face for contacting the sclera and aligning the axes of a plurality of beams' propagation toward the meshwork, and a laser energy source having a wavelength range appropriate for penetration to the meshwork. Further, the invention includes an optional dosimetry control system for terminating or controlling energy delivery based on feedback signals from a temperature sensor array in the working face.

The working face has a $1^{st}$ corneo-spherical receiving portion and a $2^{nd}$ sclero-spherical receiving portion for positioning the face in contact with the globe with a footprint dimension that is large enough to stabilize the working face at a proper treatment angle. Within the working face are a plurality of light beams emitters connected with fiber optics to the laser source. The emitter axes at which the beams propagate are provided at a predetermined angle relative to the $1^{st}$ and $2^{nd}$ part-spherical receiving portions of the working face, for example a tangent to the sclera.

Research and modeling indicates that the preferred wavelength ranges for opto-thermal biostimulation of the trabecular plates lie in the near-infrared portion of the spectrum, preferably in ranges of about 1.30 $\mu$m to 1.40 $\mu$m or about 1.55 $\mu$m to 1.85 $\mu$m. It is believed that absorption coefficients related to the above ranges, or a subset of the such ranges, will prove best suited for such trabecular meshwork stimulation. The depth of absorption of such wavelength ranges will extend through most, if not all, of the thickness of the sclera (750 $\mu$m to 950 $\mu$m). For the proposed method of trabecular biostimulation, the targeted region is elevated in temperature to a range between about 40° C. to 55° C. for a period of time ranging from about 1 second to 120 seconds or more. More precisely, the desired range would be between about 40° C. to 50° C. for such time periods. The optimal therapeutic effects will result from a balance of appropriate light energy wavelength, power level, exposure duration, together with the thermal absorption characteristics of the heat-sink working face.

The light-mediated trabecular biostimulation techniques proposed herein differ greatly from other common laser-tissue interactions. The proposed technique develops only low energy densities in the absorbing medium as can be seen in the chart of FIG. 4C where various temperature levels indicate different effects on tissue. Such biostimulative effects are caused by a photoexcitation modality proposed herein which differs significantly from typical modalities of laser-tissue interactions: the photocoagulation and photodisruption modalities. In the photocoagulation modality, photons elevate tissue temperatures sufficient to coagulate, denature, shrink, desiccate or cause thermolysis of tissues such as in ALT and SLT (see FIG. 4B). In the photodisruption modality, photons of a light energy beam disrupt the chemical bonds of atoms or molecules making up the medium, with the end result being that the medium is vaporized as indicated in FIG. 4B. In the present invention, the objective is to elevate meshwork to temperatures well below those used to practice the photodisruption or photocoagulation modalities. The photoexcitation modality proposed herein uses far less energetic photons in the above-described ranges which will cause atoms and molecules in the meshwork or aqueous AQ engulfing the meshwork to vibrate or resonate. The excitement or resonant effect will elevate the temperature within the absorbing medium (meshwork) without disrupting any intramolecular or intermolecular chemical bonds, such as would occur temperatures above about 60° C. which can cause denaturation of tissue.

The dosimetry control component of the invention can be adapted to control exposure duration, power levels and timing of energy delivery in various operational modes. A basic mode of operation can follow a pre-set program of timing and power based on treatment experience. A preferred operational mode is based on a feedback-control system that receives signals from a thermal sensor in the working end of the device. Another preferred operational mode is based on a feedback-control system and a beam sequencing controller that sequences beam delivery between or among non-adjacent emitter locations to optimize temperature elevation in the meshwork while minimizing temperature elevation in the anterior and mid-sclera.

In general, the present invention advantageously provides a system having an arrangement of a plurality of n spaced-apart beam emitters in a radius that corresponds to that of the trabecular meshwork of a patient's eye for transsclerally treating an angular portion of the meshwork with a single energy delivery.

The invention advantageously provides a device having a working face with geometry and part-spherical receiving forms for receiving portions of a patient's cornea and sclera to insure the light energy beams are directed toward the trabecular plates.

The invention advantageously provides a device having n lens elements to insure that the light energy beams penetrate and are absorbed substantially about the region of the trabecular meshwork.

The invention advantageously provides a device and method for creating a reverse thermal gradient in the sclera by lowering the temperature of the anterior surface of the scleral with a heat-sink working face to protect the scleral epithelium.

Additional features and advantages of the device and method of the present invention will be understood from the following description of the preferred embodiments, which description should be taken in conjunction with the accompanying drawings.

BRIEF DESCRIPTION OF THE DRAWINGS

FIG. 4B is a chart indicating laser-tissue effects at various temperature levels in tissue, including the modality of photoexcitement proposed herein; the photocoagulation modality wherein tissue is caused to coagulate, denature or shrink; and the photodisruption modality wherein tissue is vaporized.

FIG. 12A indicating the thermal effect of a light beams' incidence on tissue at the instant of energy absorption; FIG. 12B indicating the thermal effect of the light beams a number of nanoseconds later.

DETAILED DESCRIPTION OF THE INVENTION.

Figure 5:
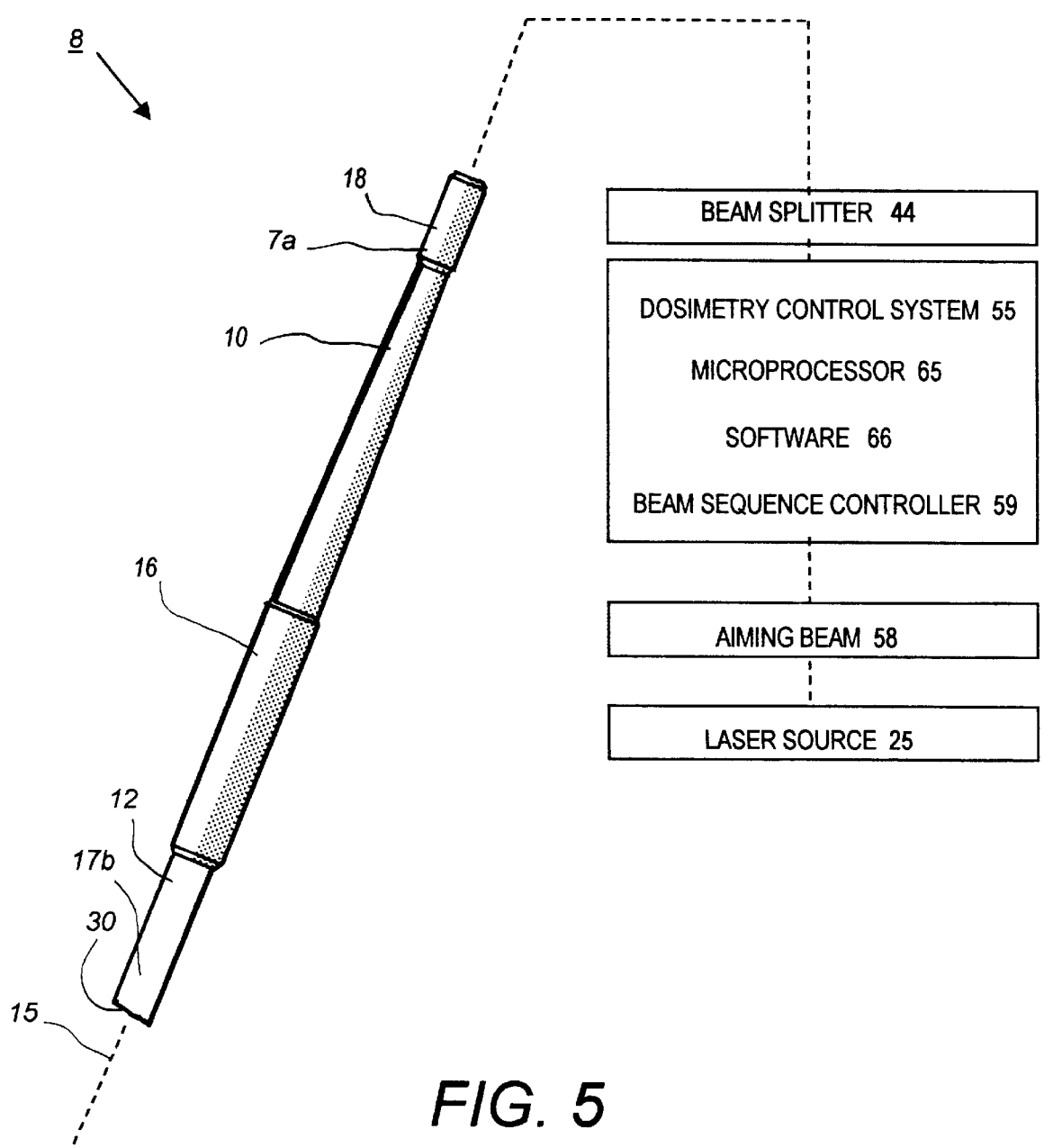
FIG. 5 is a perspective view of the handpiece of the present invention together with a block diagram of the components and control systems of the invention.

Referring now to FIG. 5, the laser system 8 with handpiece 10 of the present invention is shown which is adapted for the novel technique of elevating the temperature of a patient's trabecular meshwork for biostimulation purposes. The system of the invention, for convenience, may be at times referred to as an $OT^3$ system ("OT-Cubed system") for the practiced technique of opto-thermal transscleral trabeculoplasty.

The present invention includes cooperating means for projection of energy beams at particular penetration angles in particular spatial locations on the anterior surface of the sclera, together with wavelength means for transscleral penetration of such energy beams to reach the patient's trabecular meshwork. The $OT^3$ device thus provides (i) a working end with particular geometry for propagating light beam(s) relative to the sclera's anterior surface, (ii) a laser energy source operating within selected wavelength domains, and (iii) an optional dosimetry control system for controlling (or terminating) laser energy delivery based on a temperature feedback signals. These systems and aspects of the invention will be described in order below, and subsequently in their use in performing the technique of the invention in stimulating cellular and other processes of the trabecular meshwork.

1. Working End Beam Propagation Geometry

As can be seen in FIG. 5, handpiece 10 comprises a working end portion 12 that extends along axis 15 and which is coupled to body portion 16. The working end 12 is fabricated of any suitable transparent material, such a transparent medical grade plastic. The body is formed of any suitable material such as metal or plastic and is adapted for gripping with a human hand. Preferably, working end 12 and body 16 are of inexpensive and disposable injection-molded parts. The body 16 has proximal and distal ends, indicated at 17a and 17b, respectively, with end 17a having a detachable coupling 18 for connecting fiber optic cable 20 thereto for operative connection to laser energy source 25 described below.

Figure 6:
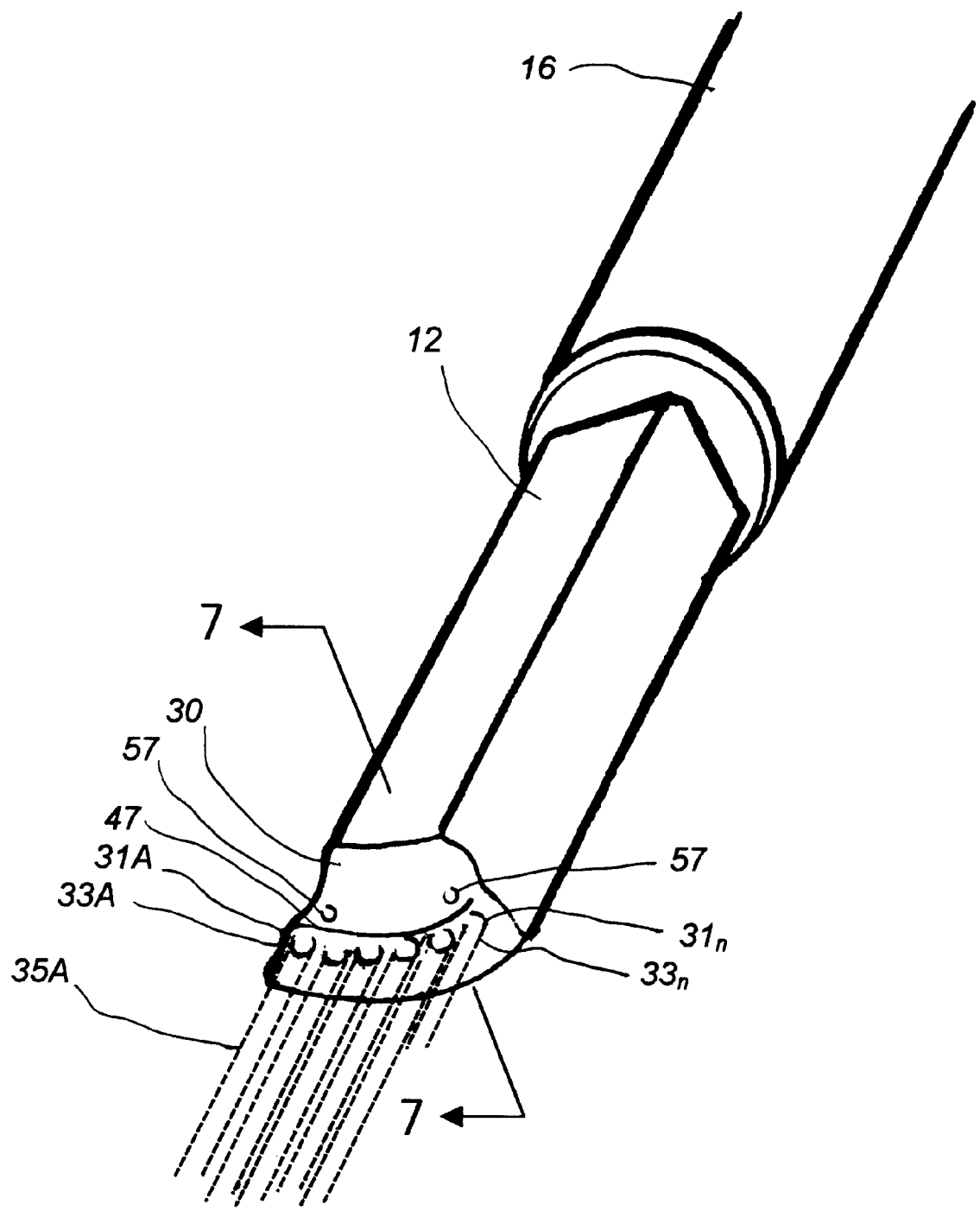
FIG. 6 is an enlarged perspective view of a the distal working end of the handpiece of FIG. 5 depicting a plurality of emitter locations and light energy beams emitting therefrom.
Figure 7:
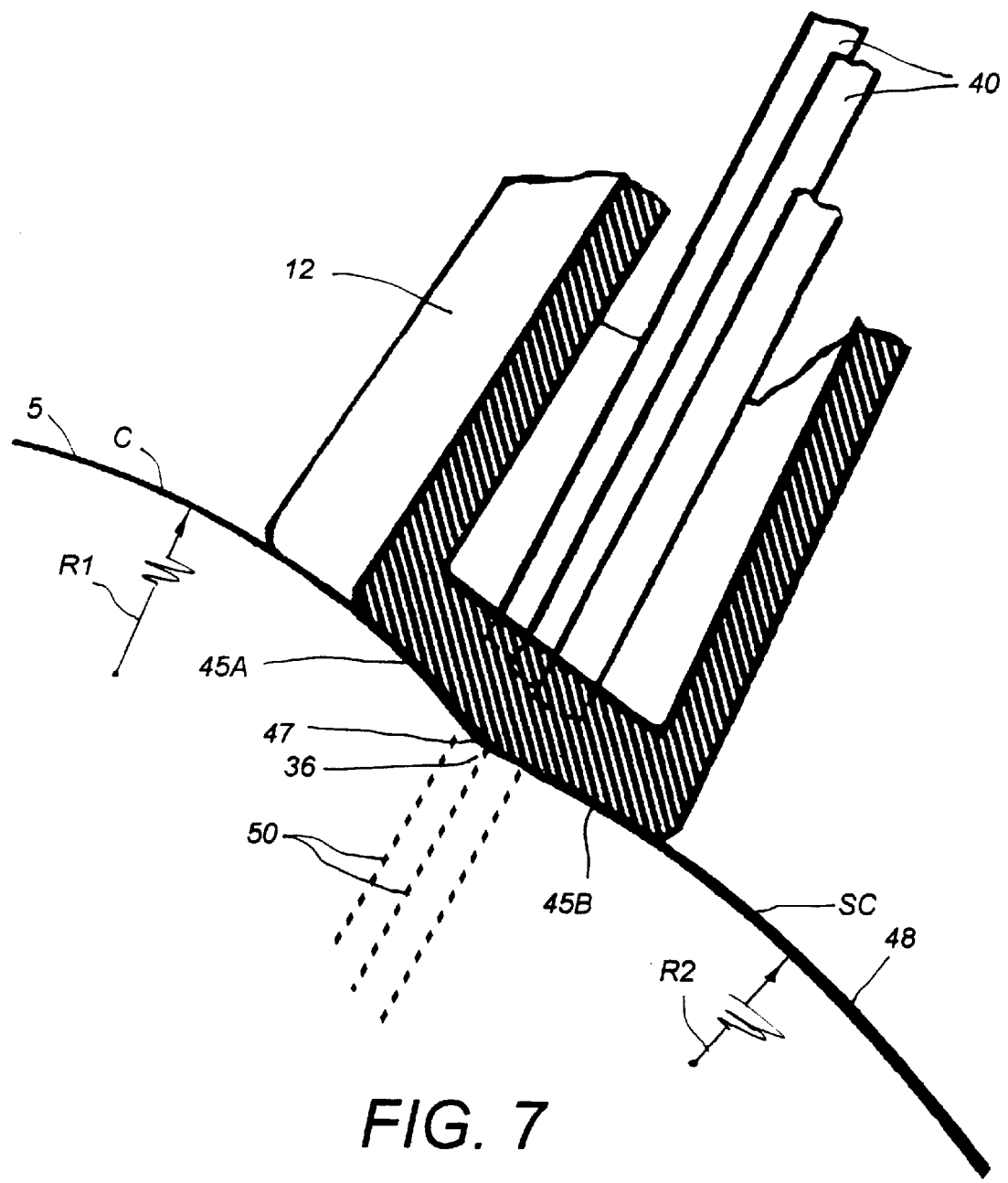
FIG. 7 is a sectional view of the working end of FIG. 6 taken along line 7—7 of FIG. 6 showing particular working end geometry.
Figure 8:
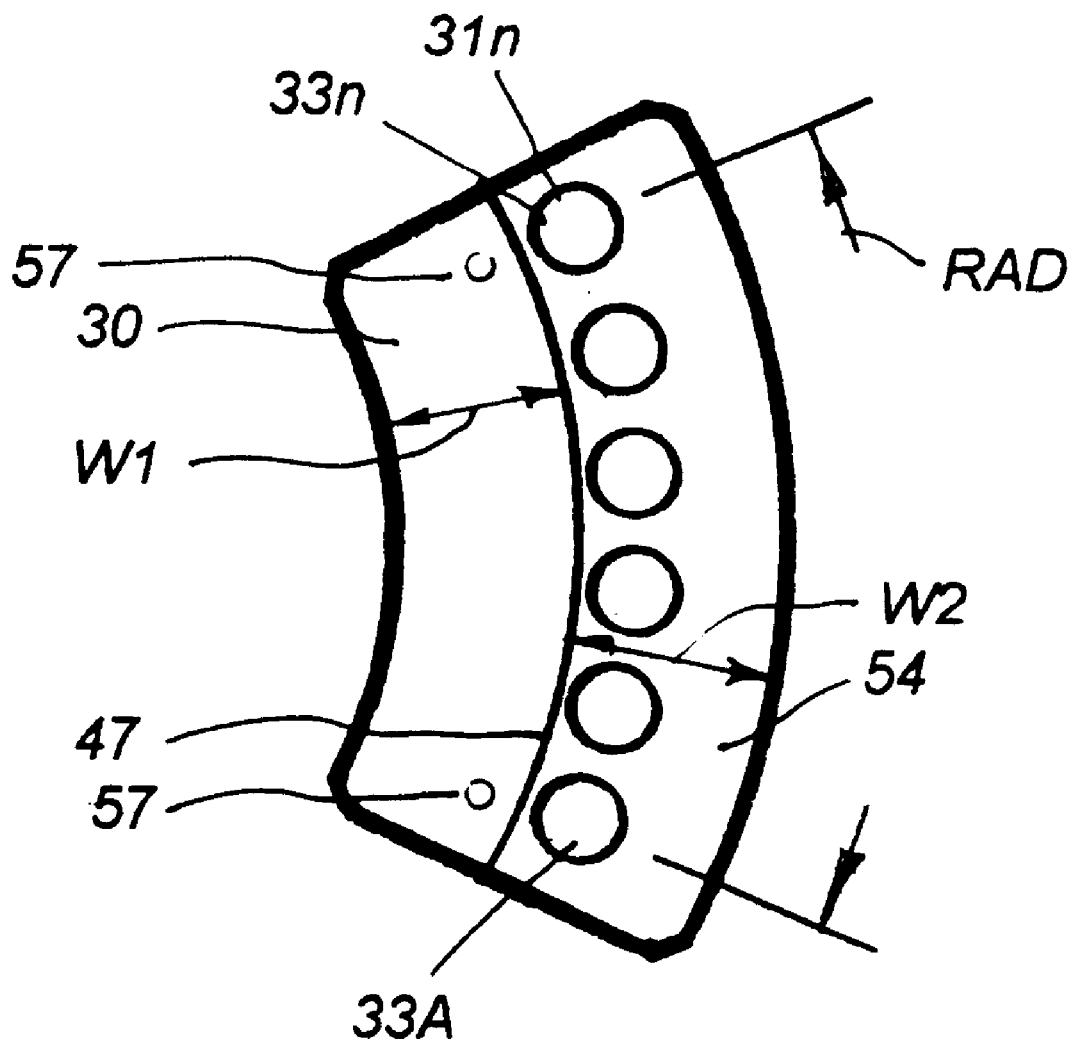
FIG. 8 is a plan view of working end of FIG. 6 showing other particular working end geometry.
Figure 9:
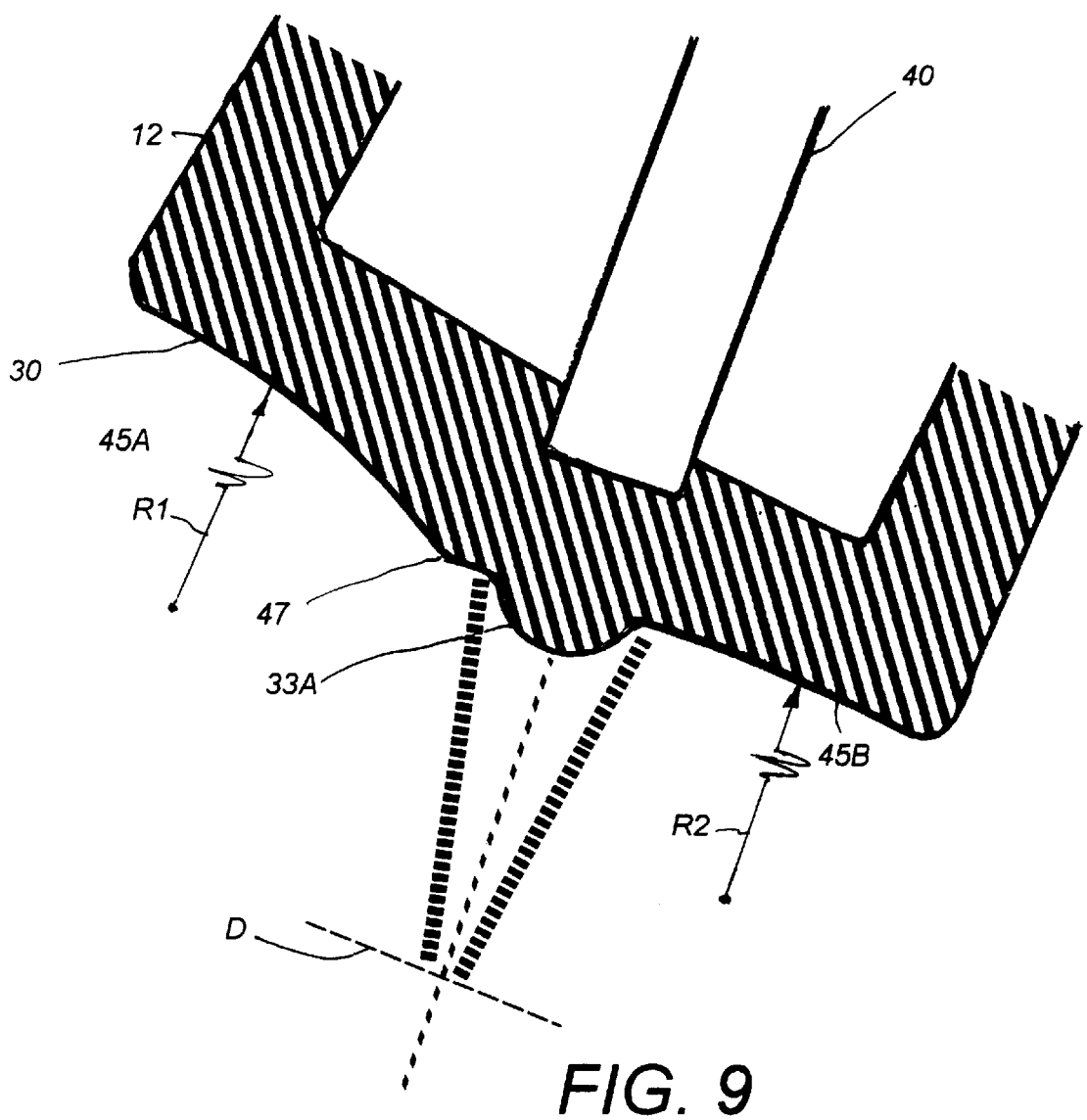
FIG. 9 is an enlarged sectional view of the working end of FIG. 7 showing a lens element.

FIGS. 6–8 show perspective, sectional and plan views of working face 30 of working end 12 with a plurality of emitter locations 31A–31n and lens elements 33A–33n from which beams 35A–35n are be emitted. The preferred embodiment shows a plurality of 6 emitter locations 31A–31n, but it should be appreciated the number of emitters may range from about 1 to 10 per any 10° to 45° of radial angle distance RAD of working face 30 (FIG. 8) described below (i.e., n=1 to 10). The number of emitter locations 31A–31n also will vary depending on selected beam diameter described below. FIG. 6 shows that individual optic fibers 40 (collectively) are connected by any suitable means (e.g., cement or a clamping mechanism) at each emitter location and more particularly to each lens element 33A–33n. FIG. 9 shows an enlarged sectional view of a lens element 33A which is adapted as a plus-type lens to converge the beam generally at depth D which is about the depth of meshwork M (about 750 $\mu$m to 950 $\mu$m) as is known in the art. It should be appreciated that the lens element 33A is represented as a part-hemispheric lens but that any flat field or convergent lens may be appropriate for optostimulation of the meshwork M and falls within the scope of the invention.

The light beams 35A–35n may be generated and emitted by the emitters from any suitable source of light, either coherent or non-coherent, and may be from a pulsed or CW laser source in the wavelength domain described below. It should be appreciated that the term "emitter" is used herein to describe the location or point at which beams 35A–35n are emitted from working end 12 and lens elements 33A–33n into the sclera, and as such, the emitter is considered to be a combination of elements including, but not limited to, the laser source 25 together with optics, fiber optics, lenses, mirrors, filters, splitters, combiners, energy attenuators, beam shapers and other arrangements operatively connected between the laser source 25 and the lens elements 33A–33n. FIG. 5 shows beam splitter 44 that is known in the art for splitting output from one or more light sources 25 to pump the light energy into each individual optic fiber 40.

Figure 10:
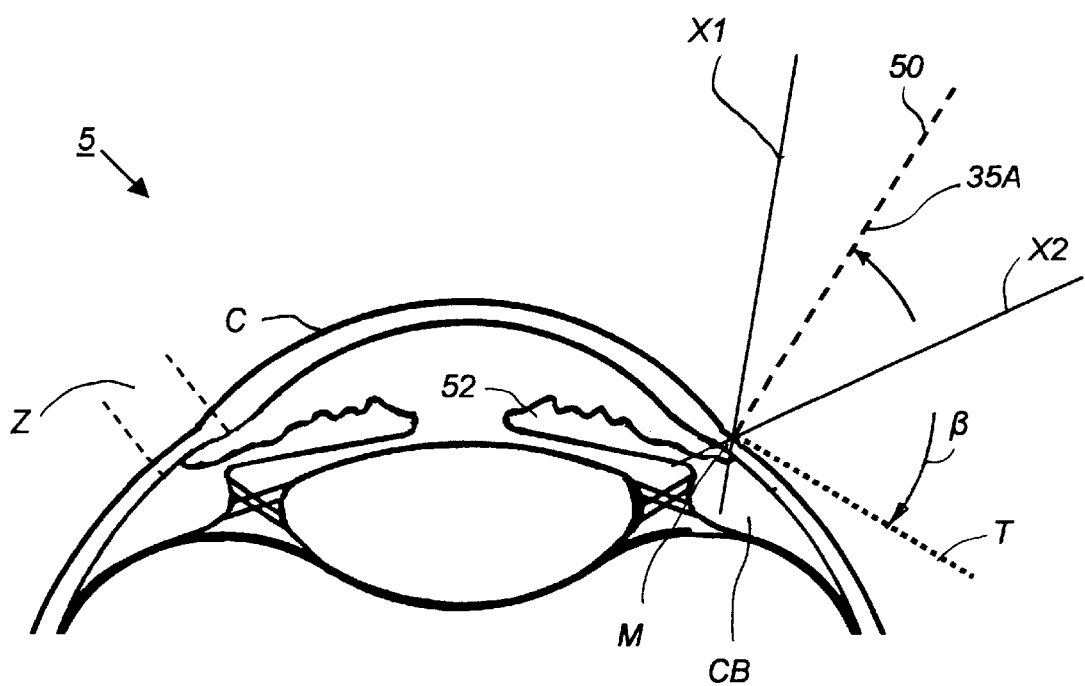
FIG. 10 is an enlarged sectional view of a sclera and cornea and showing various transscleral angles-of-attack.
Figure 11:
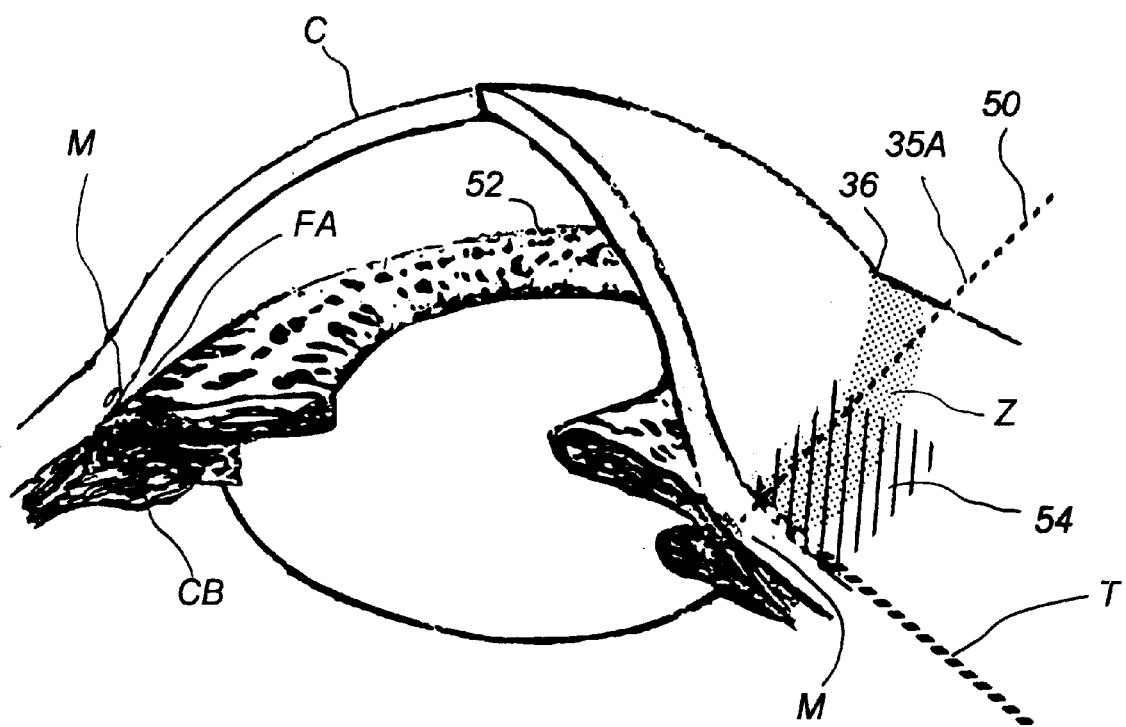
FIG. 11 is a partial sectional view of an eye showing the footprint of the working end of FIGS. 6, 7 & 8.

Turning now to FIGS. 10–11, very particular beam-angle propagation means are formed into working face 30 of working end 12 that comprises a balance between several considerations and several potential transscleral angles-of-attack to reach the trabecular meshwork M. Referring back to FIG. 7, the working face 30 in its treatment position is adapted to interface with globe 5 generally in surface contact with three portions of the globe: the sclera SC, the limbus 36 and the cornea C. In other words, the working face has a first corneal-spherical receiving portion 45A and a second scleral-spherical receiving portion 45B with annular limbus-interface portion 47 therebetween. The limbus 36 herein is defined as the particular annular transition region from 0.5 mm. to 2.0 mm. between the sclera and cornea. Further, the working face 30 extends a minimum radial angular distance RAD when measured in degrees as will be described below (see FIG. 8). Thus, the footprint dimensions of working face are large enough to stabilize the working face 30 against the globe, as well as for functioning as a heatsink as described below.

FIGS. 10–11 show that a particular limited range of angles-of-attack (or beam propagation) relative to anterior surface 48 that is indicated to reach meshwork M. Among the considerations for determining the most preferable angle-of-attack are (i) the reduction of incident beam reflection off the anterior surface 48 of the sclera SC; (ii) the reduction of unnecessary photon scattering in the mid-sclera 53, and (iii) the elimination of any angle-of-attack that might align with anatomic structures that one would not want to irradiate unnecessarily. To meet these objectives, the working face 30 is formed with a geometry for angular positioning the axes 50 (collectively) of propagation of beams 35A–35n within a defined angle—for example angle β which measures the angle between an axis 50 of beam propagation and a tangent T to the sclera in an incident zone Z outside the limbus centerline 51. In other words, axis 50 extends from the zone Z in which a light beam penetrates the anterior 48 of the sclera to hit meshwork M. As can be seen in FIG. 10, any beam propagation at other angles along other lines (e.g., lines $X_1$ or $X_2$) that are more oblique relative to tangent T may cause photonic energy to be absorbed in undesirable locations like ciliary body CB or iris 52 and thus damage tissue outside the meshwork M. The correct beam propagation angle β can be defined in a number of different geometric manners relative to surfaces, radii, axes etc. of globe 5, and for that reason the ranges of radii of curvature of a normal globe are shown in FIG. 10. Preferably, as shown in FIG. 8, beam angle β is within a range of about 10° on either side of a line drawn perpendicular to tangent T in the zone Z of the sclera and limbus. Incident zone Z has in lesser diameter of about 0.0 mm. to 0.5 mm. from the centerline 51 of limbus 36 and an outer diameter to 3.0 to 5.0 mm. from the centerline 51 of the limbus 36. Thus, the working end geometry in its "contact position" or "treatment position" against globe 5 orients beams 35A–35n to (i) allow about the least distance of travel possible through the sclera SC to the meshwork M to correspond to wavelength domains described below; (ii) allow reduction of photon scattering and heat within the mid-sclera 53 by minimizing the beams' propagation length through the sclera; and (iii) allow light beams 35A–35n delivery at close to a 90° angle relative to anterior surface 48 of sclera SC to reduce surface photon reflection.

Of particular interest to the invention, the compound curvatures 45A and 45B (first corneal-spherical receiving portion 45A and second scleral-spherical receiving portion 45B) of working face 30 allow the ophthalmologist to gently fit the working face against the globe 5 about the corneal-scleral junction to insure the optimal beam spatial location and beam angle-of-attack. The ophthalmologist first may move the working face laterally back and forth as shown in arrow A1 in FIG. 10 until it fits comfortably against the eye. Thereafter, the ophthalmologist may tilt working face 30 against the curvature of the sclera and cornea as indicated by arrow A2 as shown in FIG. 10 to establish the correct angle β relative to globe 5. In the previous view of the working face in FIG. 7, it can be seen that first part-spherical receiving form 45A has a meridional or first cross-sectional radius R1 of about 6.4 mm. to 7.8 mm. which represents a meridian of corneal curvature. The working face 30 has second part-spherical receiving form 45B with a second cross-sectional radius R2 of from about 8.0 mm. to 12.0 which represents a meridian of scleral curvature (or greater) with the forms 45A and 45B meeting along partial annular junction 47. The width of first part-spherical receiving form 45A may range from about 0.5 mm. to 4.0 mm., indicated at W1 in FIG. 8. The width of second part-spherical receiving form 45B may range from about 2.0 mm. to 5.0 mm., indicated at W2 in FIG. 8.

FIG. 8 shows a plan view of working face 30 indicating that it is adapted to extend a particular angular or radial angle distance RAD around globe 5 and is shown in this preferred embodiment with a radial extension RAD of about 60° out of 360°. It should be appreciated that other embodiments are possible and fall within the scope of the invention and such radial extension may range between about 10° and 180° (see FIG. 8). In terms of circumferential dimensions, the dimension along partial annular junction 47 of working face may range from about 2.5 mm. to 2.0 cm. The footprint 54 defining the surface area of working face 30 preferably has an area of at least 20 mm.$^2$ to meet the requirements of stabilizing the working face against globe 5 to provide the correct angle of beam propagation, and to provide sufficient heat absorption characteristics for any of the materials of working face described herein. More preferably, the footprint 54 of working face 30 has an area of at least 40 mm.$^2$ to meet above requirements. Still more preferably, the footprint 54 of working face 30 has an area of at least 60 mm.$^2$ to meet such requirements.

The dosimetry control system 55 will be described in detail below in Section 3. Some aspects of the dosimetry control system can be fed by a signal from sensors 57 (collectively or sensor array) in working face 30. Therefore, referring back to FIGS. 6 & 8, it can be seen that sensor array 57 is provided which comprises thermisters or thermocouples carried in a spaced apart relationship close to lens elements 33A–33n in face 30. The sensors may be in actual contact with the sclera SC or may measure the temperature of the material of face 30 that is in contact with the sclera. Each thermocouple or thermister (a temperature sensor that has resistances that vary with the temperature level) is any suitable type known in the art and may consist of paired dissimilar metals such as copper and constantan which form a T-type thermocouple.

Referring back to FIG. 5, a block diagram of the controllers of the system 8 is included and further shows a visible aiming beam (e.g., a HeNe laser) indicted at 58 operating at 630.8 nm or any other suitable visible laser wavelength. The system includes dosimetry control system indicated at 55 and optional beam sequence controller 59, which computer controllers are adapted to operate in cooperation (as will be described below) to control the power of beams 35A–35n, as well as the timing, of laser energy delivered from laser source 25.

2. Laser Source Wavelength Selection

The preceding section described the working end geometry or positioning mechanisms of the novel $OT^3$ device to insure that the physician can easily and consistently locate the working face 30 in suitable "treatment positions" on or about the anterior scleral surface. This section and FIGS. 12A–12B describe the means provided by the invention for controlling penetration of light beams 35A–35n beneath the anterior scleral surface 48 to provide the desired photon absorption within the trabecular meshwork M. The biostimulative effect is caused by the beam's photonic energy being absorbed and exciting (or vibrating) molecules within the meshwork, and for that reason the energy delivery effect may be called herein a photoexditation modality to distinguish it from various high-energy laser delivery modalities described in the section above titled "Summary of the Invention".

Figure 12A:
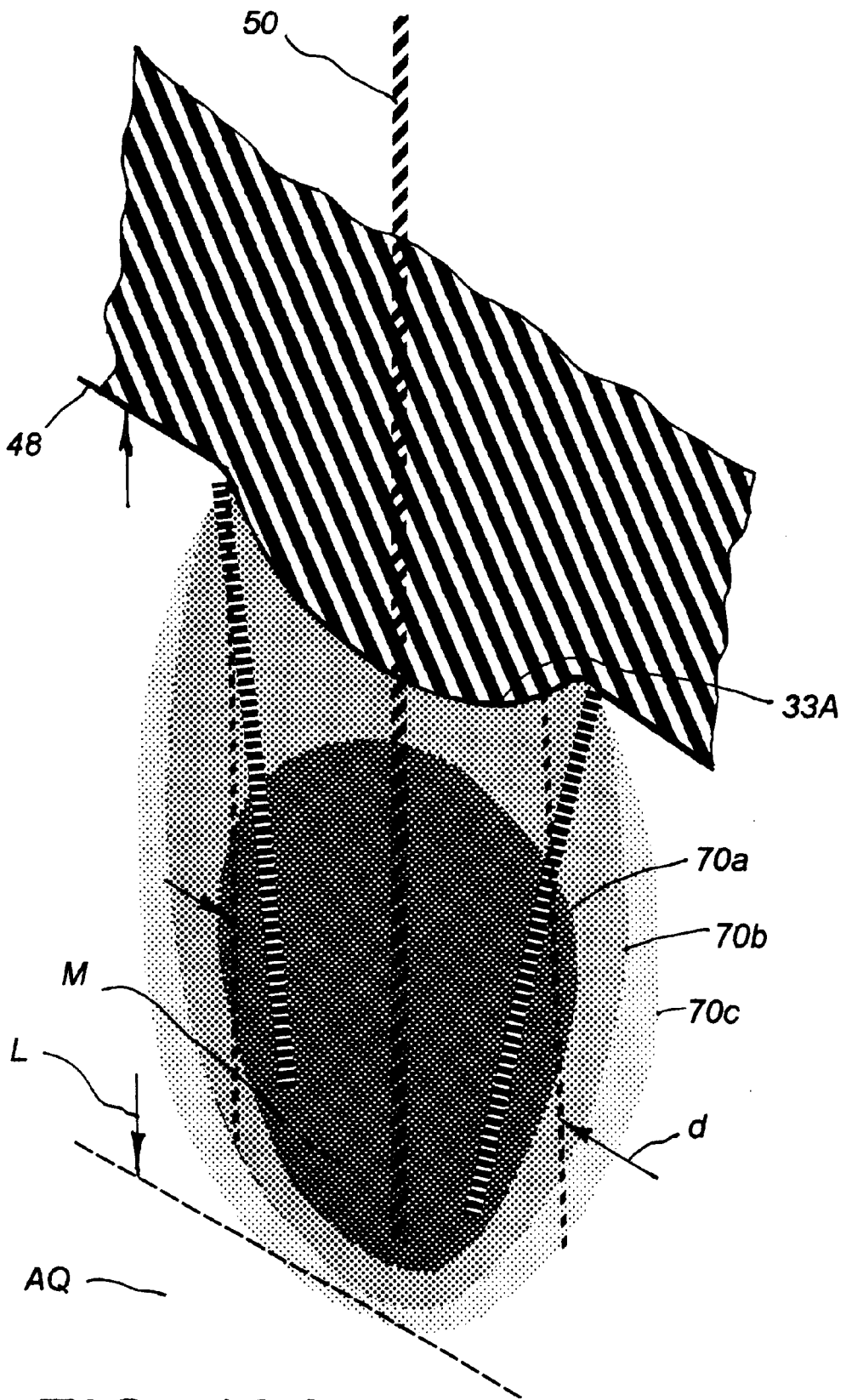
FIGS. 12A–12B are sectional representations of a patients sclera and trabecular meshwork regions depicting a manner of utilizing the apparatus of FIG. 5 in performing a method of the invention in elevating the temperature of the meshwork.

Turning back to FIG. 10, the perspective and partial sectional view of globe 5 shows the beams 35A–35n incident within zone Z at a particular moment in time that represents a technique of the invention. FIG. 11 also shows the approximate location of zone Z over the trabecular meshwork with the footprint 54 of working face 30 and the working end 12 in phantom view in a second treatment location. FIG. 12A illustrates an enlarged full-thickness sectional view of the sclera SC and meshwork M taken along an arc-like section of FIG. 11. Sclera SC has a number of layers including epithelial layer 60 with the total scleral thickness ranging from about 750 $\mu$m to 950 $\mu$m.

The object of the invention, transscleral opto-thermal biostimulation, requires identification of a specific light wavelength domain that may be produced by laser source 25 to penetrate substantially to the depth of about 750 $\mu$m–950 $\mu$m. As background, when light energy is incident upon tissue, five effects may result: (i) the beam, or some or all of the photons thereof, may be reflected off the tissue surface; (ii) the photons thereof may be transmitted entirely through the tissue medium, (iii) the photons thereof may be absorbed along the beam's propagation in the tissue medium by absorption within a chromophore, (iv) the photons thereof may be absorbed along the beam's path of propagation by varied processes of scattering; or (v) some of beam may be scattered within the tissue beyond the region of the beam's path as it propagates within the tissue medium.

To provide photon absorption to a depth in tissue of about 750 $\mu$m–950 $\mu$m, two of the above factors are of interest to cause biostimulation of the trabecular meshwork M. Of particular interest are the photon absorption effects (i) and (iv) listed above. Preferably, the photons of the energy beams 35A–35n will be absorbed by the $H_2O$ content of the meshwork acting as a chromophore, and also be absorbed by photon scattering processes, thus elevating meshwork temperature. (As noted previously, photon reflection off anterior surface 48 is minimized to the extent possible, and deeper absorption is allowed, by orienting axes 50 of the beams substantially perpendicular to the anterior scleral surface which relates to beam incident effect (i) above).

Figure 1A:
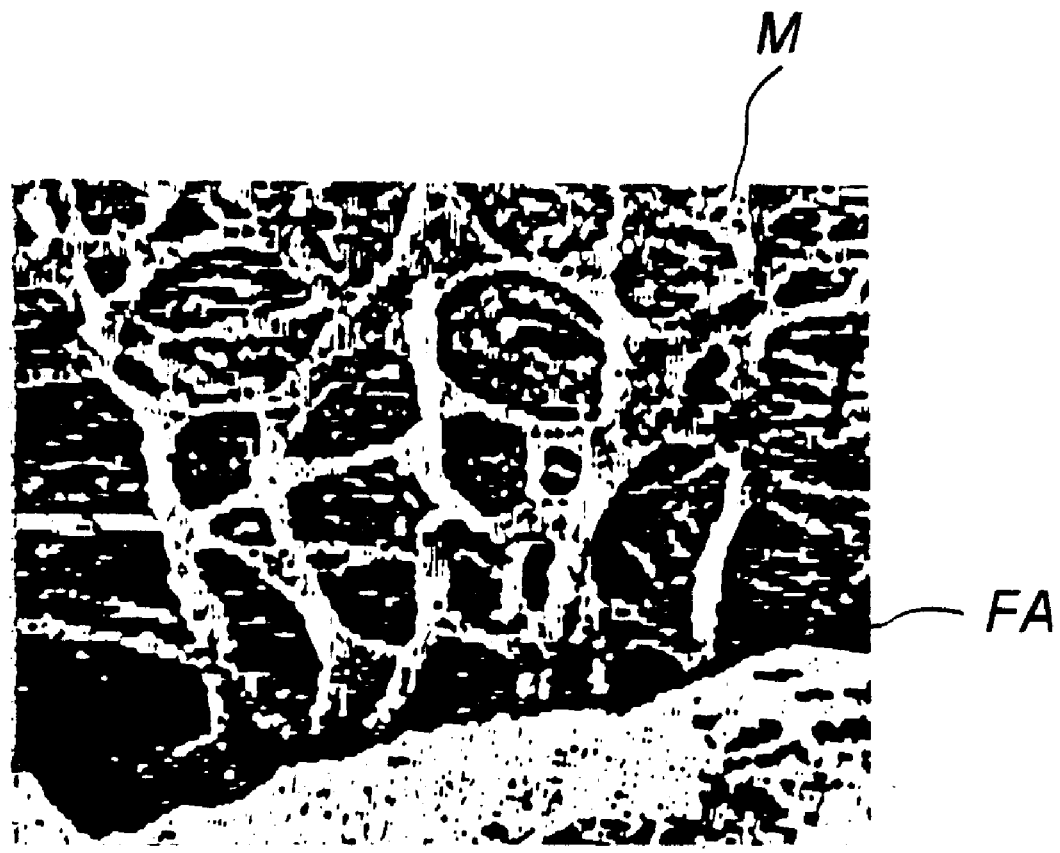
FIG. 1A is an electron micrograph of the trabecular meshwork of a patient's eye.
Figure 1B:
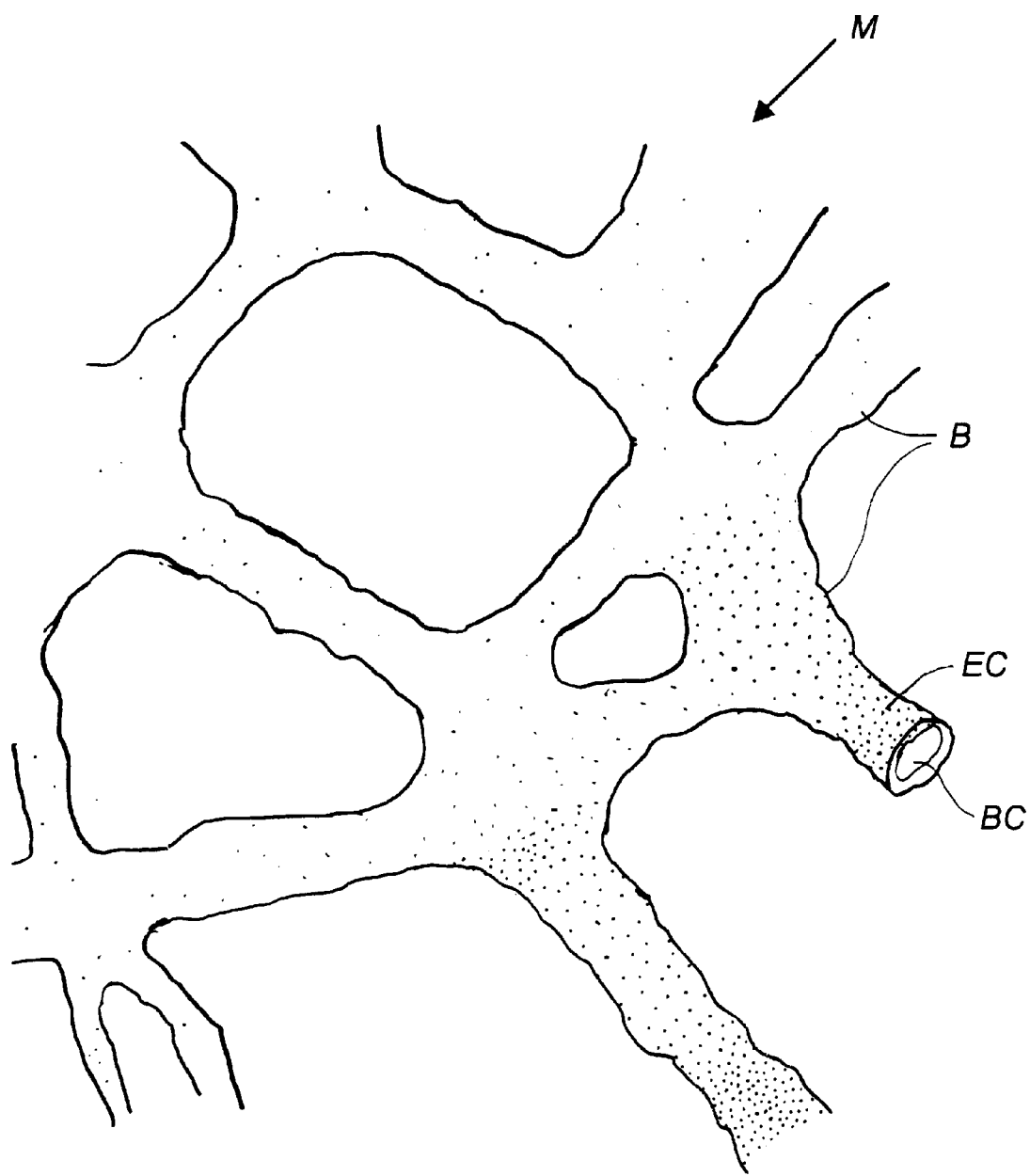
FIG. 1B is an enlarged electron micrograph of the trabecular meshwork of FIG. 1A with a schematic sectional view of a trabecular beam.
Figure 1C:
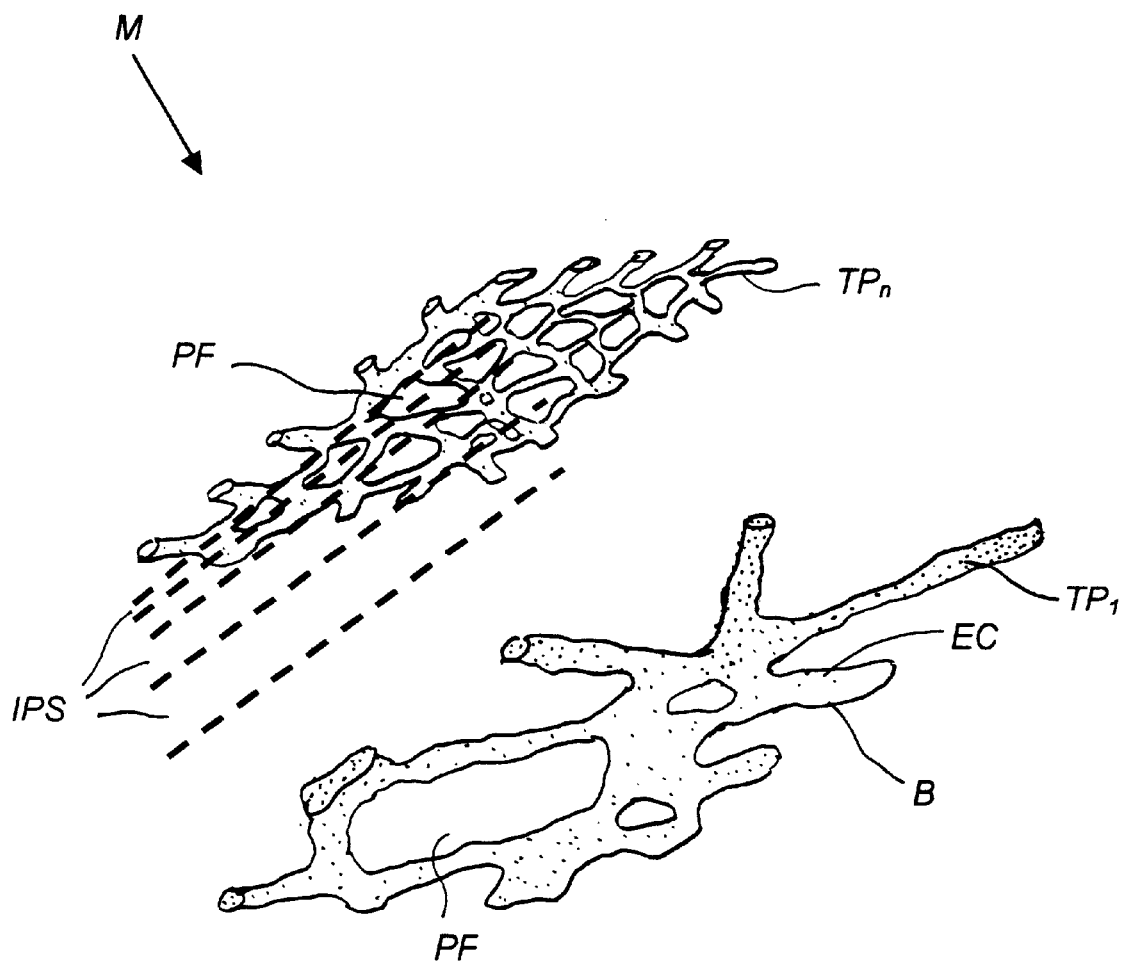
FIG. 1C is a sectional representation of the trabecular plate layers of meshwork of FIG. 1A.
Figure 1D:
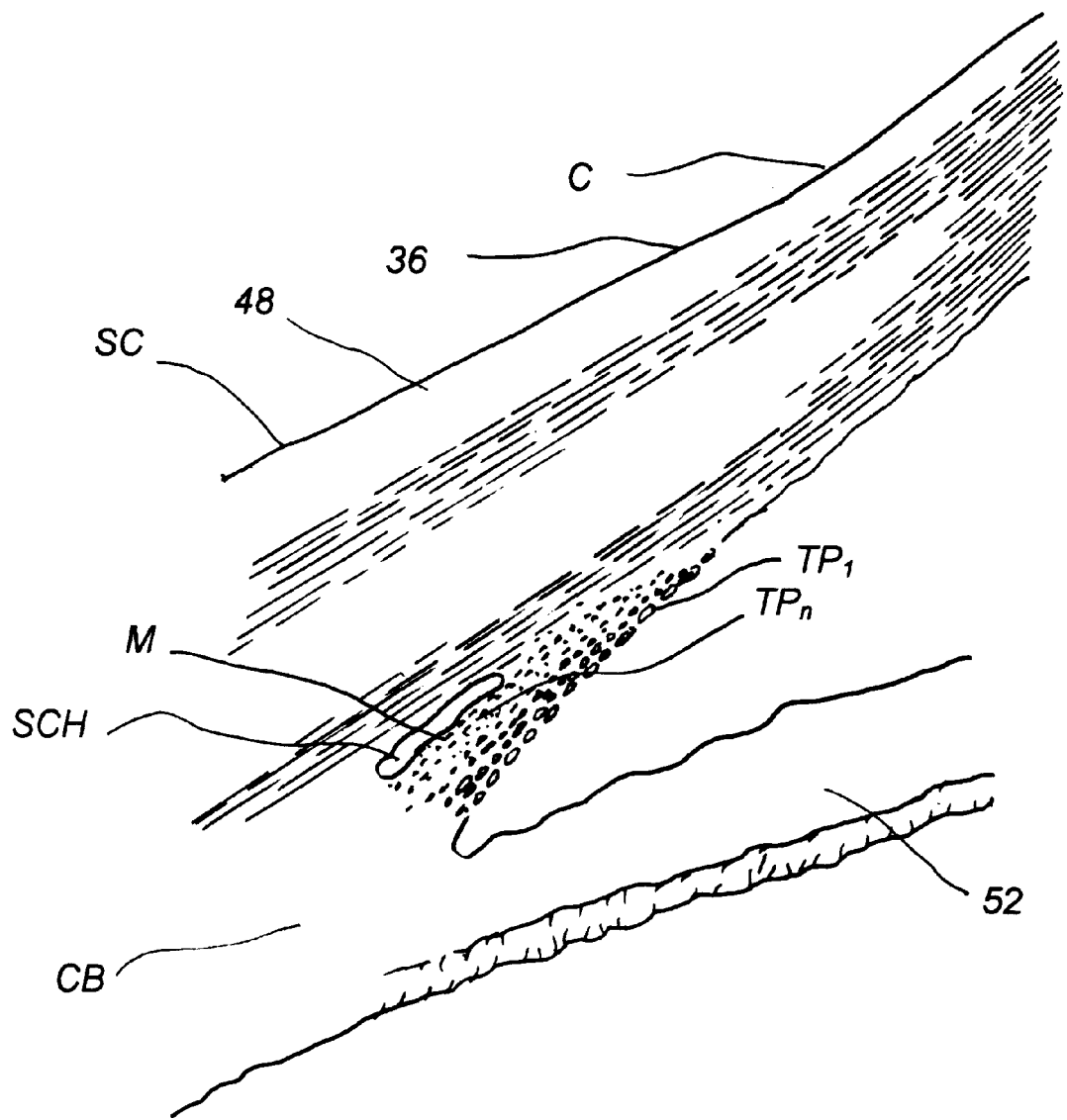
FIG. 1D is a sectional view of a patients' eye or globe showing the location of the trabecular meshwork.
Figure 2A:
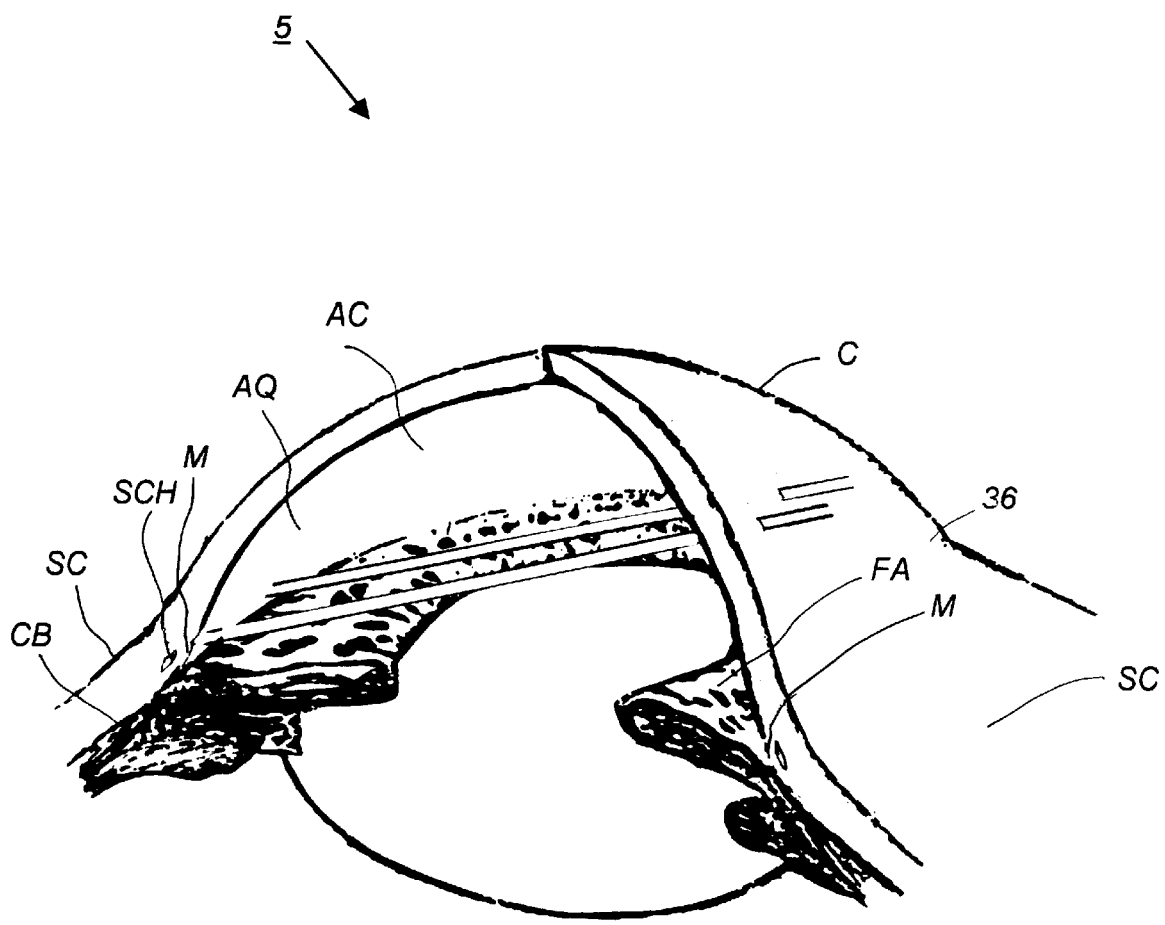
FIG. 2A is a view of a prior art method of laser treatment of trabecular plates.
Figure 2B:
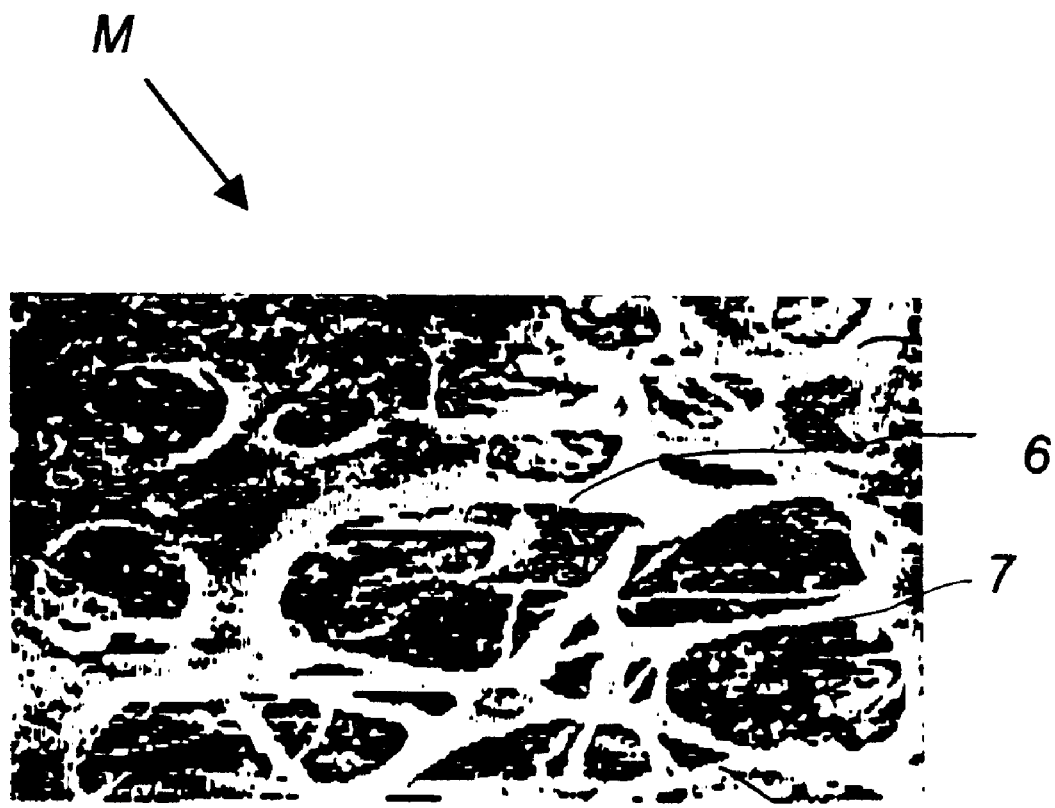
FIG. 2B is an electron micrograph of a laser melt of trabecular plates in the prior art method of FIG. 2A.
Figure 3:
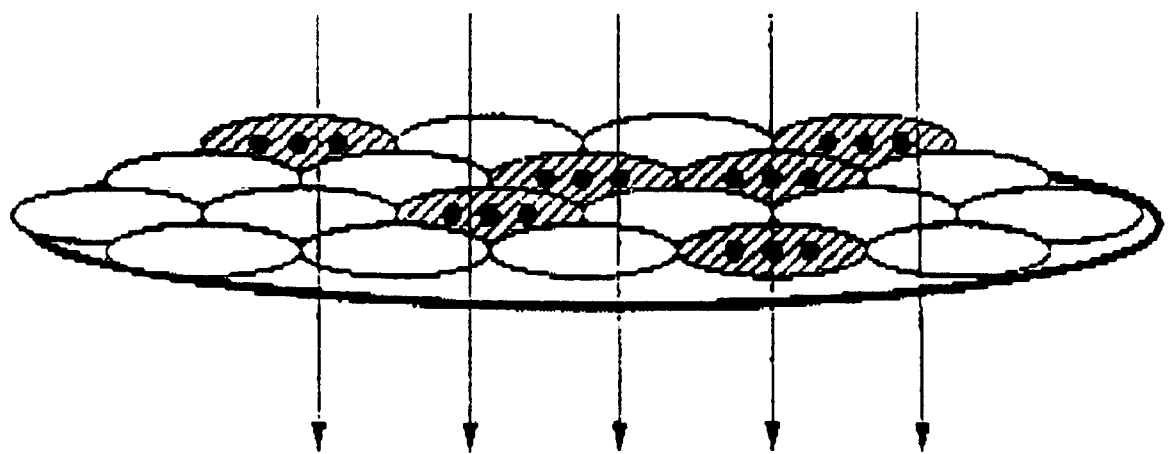
FIG. 3 is a schematic view of another prior art method of laser treatment of a trabecular plate.
Figure 4A:
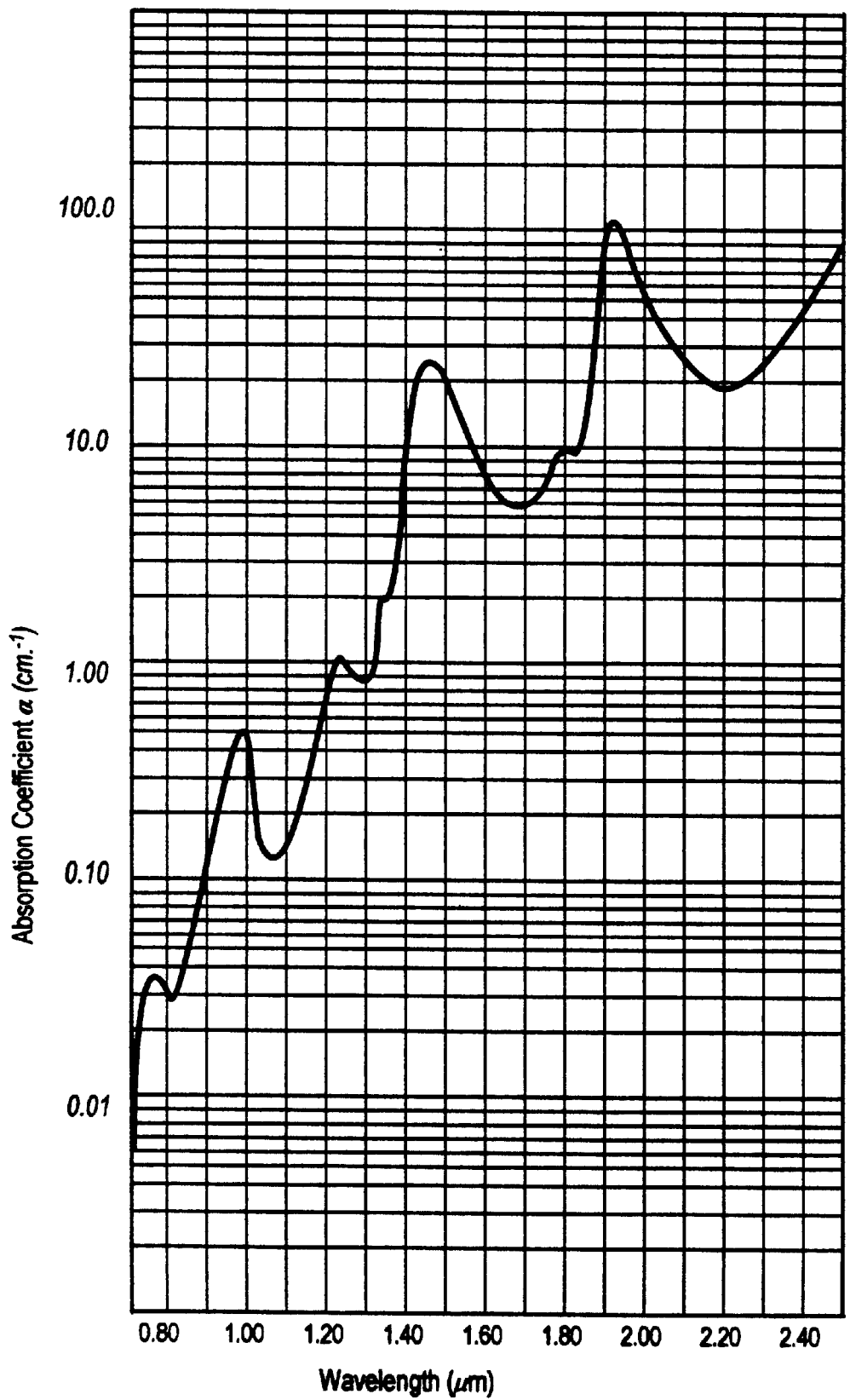
FIG. 4A is a graph showing light wavelengths with absorption coefficients in water.

Since the sclera is about 75%–80% water with little or no cellular pigmentation, FIG. 4A is relevant as it depicts an absorption coefficient of water as a function of wavelength ($\lambda$). As can be seen in FIG. 4A, the absorption coefficient of water varies by a factor of about 10,000,000 from a peak light transmission where $\lambda$=500 nm (not shown) in the visible spectrum to peak light absorption where $\lambda$=at 2.8 $\mu$m in the infrared portion of the spectrum. Tissue research and mathematical modeling of various wavelengths indicates that the preferred wavelength range for light-mediated meshwork biostimulation lies in the near-infrared, the laser source 25 preferably operating at a wavelength ranging from about 1.30 $\mu$m to 1.40 $\mu$m or from about 1.55 $\mu$m to 1.85 $\mu$m. The wavelength ranges correspond to an absorption coefficient ($\alpha$) in $H_2O$ ranging between about $\alpha$=2.0 $cm^{-1}$ to 10.0 $cm^{-1}$, which is similar to the sclera. Such a range of absorption coefficients would result in the photonic energy being absorbed to a depth of about 750 $\mu$m to 1100 $\mu$m—in other words the depth of the trabecular meshwork or slightly beyond. It is not important if the absorption is somewhat deeper than the meshwork, for the aqueous AQ will absorb or extinguish the energy beam. Unlike ALT and SLT wavelengths that are absorbed by a pigment (melanin) or chromophore in the meshwork, the proposed wavelengths rely on $H_2O$ as the chromophore which is in the trabecular plates TP and the aqueous AQ which allows a substantially uniform temperature elevation in the entire region of the meshwork for biostimulation purposes.

The temperature targeted for meshwork biostimulation is in the range of about 40° C. to 55° C. for a period of time ranging from about 1 second to 120 seconds, with the temperature inversely related to the duration of exposure. More preferably, the target temperature is within a range of 40° C. to 50° C. It would be preferable to achieve an energy profile that photoexcites the region of the meshwork without over-elevating the temperature levels in the sclera overlying the meshwork. For example, it is preferable that the opto-thermal effects do not cause excessive cell death in epithelial layer 60 or in the mid-sclera region 53. Such excessive cell death along the light beam's propagation through the sclera could induce an inflammatory response or wound healing response which would be undesirable, although not serious threat to the patient's health. Cell damage in the sclera is to be expected to some extent, but since the inventive technique is transscleral, there should be few undesirable side effects. This is to be contrasted with the trans-corneal approach of SLT which causes corneal burns in significant numbers of cases resulting in at least a transient effect on corneal clarity.

Figure 12B:
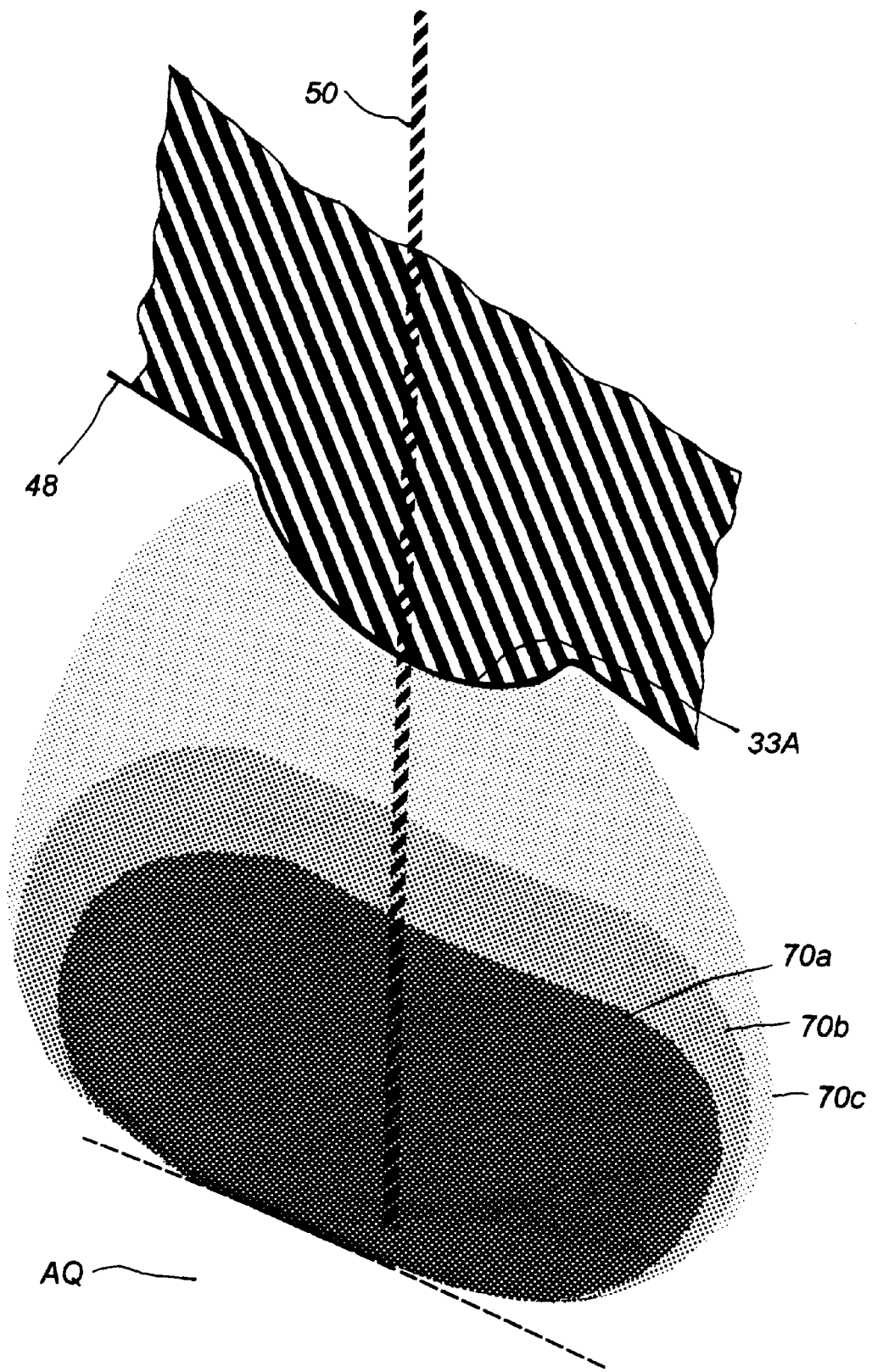

The present invention provides protection means for preventing over-elevation of temperatures in the epithelial layer 60 and the midscleral region 53, by: (i) balancing wavelength selection along with a low laser power level to penetrate the sclera; (ii) balancing exposure duration with temperature which exposure can be terminated with feedback control, and most importantly (iii) providing heat-absorption characteristics incorporated in working face 30. In other words, a transient reverse thermal gradient in the sclera can be achieved by use of the heat-sink working face 30. Due to the relatively low target temperatures, the heat-sink of even a plastic working face 30 around the lens elements will carry a significant amount of heat away from the anterior regions of the sclera. It should be appreciated that other heat-sink materials known in the art may be used for portions of the working face 30, such as sapphire, quartz or heat-absorbing ceramics (other than lens elements). FIG. 12A depicts a sectional view of the propagation of beam 35A through the sclera exactly at the moment of its incidence on anterior surface 48 with exemplary isotherms 70a–70c indicating the effects of photon absorption; FIG. 12B depicts the same scleral location in as little as several nanoseconds after energy delivery has been terminated. In particular, FIG. 12B indicates that substantially all heat has been conducted away from anterior surface region 48 of the sclera to the heat-sink with exemplary isotherms 70a–70c indicating the surface cooling effect that concentrates temperature in the region of meshwork M. Such modeling shows how a transient reverse thermal gradient (cooler at anterior surface 48 than midsclera 53) can be developed to cause thermal meshwork biostimulation without raising temperatures excessively in the anterior 48 and mid-sclera 53.

Another aspect of the $OT^3$ system for effective biostimulation of the meshwork M relates the preferred diameter of scanned beams 35A–35n to provide temperatures within the particular ranges described above. Either a CW (continuous wave) or fast pulsed laser is suitable to perform the biostimulation technique of the present invention utilizing a beam width ranging from about 25 $\mu$m to 1 mm. for reasons that can be explained by the mechanisms of heat transfer in tissue. In the preferred wavelengths described above, when the light beam is absorbed in tissue medium (both by chromophores and by photon scattering) the energy in the beam is imparted to the scleral absorbing medium along the path of beam propagation. The photonic energy that is absorbed by the medium heats the absorbing volume instantly, for example in a period ranging from femtoseconds to pico-seconds. Essentially, all of the energy in the light beam is deposited in the tissue within about one extinction length (which is directly related to the absorption coefficient $\alpha$ of the sclera). Thus, it can be calculated that a three-dimensional volume of the medium will be elevated in temperature and is dependent on (i) the beam diameter, and (ii) the extinction length of the particular wavelength (with some adjustment for photon scattering). To optimize the meshwork biostimulation, it is necessary to deposit enough energy into the absorbing volume to elevate the volume to the desired temperature range before it diffuses into surrounding tissue volumes. The process of heat diffusion, called thermal relaxation, describes such process of conduction and defines the absorbing volume's thermal relaxation time (often defined as the time over which photothermal temperature elevation is reduced by one-half). Such thermal relaxation time scales with the square of the diameter of the irradiated absorbing volume in a spherical volume, decreasing as the diameter decreases. For a cylindrical-shaped irradiated volume (see FIG. 12A) with diameter d and length L, such thermal relaxation time is determined by the lesser of the two dimensions. Thus, in the laser wavelengths and tissue absorption coefficients described above, it is preferable to have the heat thermal relaxation time in the anterior and mid-sclera as low as possible to diffuse and reduce temperature elevations in those regions. For these reasons, it is postulated that beam diameters in that range of about 25 $\mu$m to 1 mm. would be best suited for meshwork stimulation, with a similar spaced-apart dimension SA from about 25 $\mu$m to 1 mm. between the individual beams and lens elements 33A–33n (see FIG. 6).

3. Dosimetry Control System of $OT^3$ Device and Methods of the Invention

The $OT^3$ device 8 includes a dosimetry control system indicated at 55 in FIG. 5 that is adapted to control the power level of laser energy delivered through the emitter locations 31A–31n in various operational modes. In utilizing the device of FIG. 5 to perform the method of the invention, the ophthalmologist gently positions the working face 30 of the device against the patient's eye as shown in FIGS. 7, 10 & 11 above following administration of a topical anesthetic. As described above, after moving the working face laterally about the surface of globe 5 and tilting the device back and forth, the physician will have a tactile feel of the correct position of the working face, at which time he may actuate the device by means of a footpedal (not shown) or any other suitable trigger mechanism to deliver laser energy under a number of different optional operational modes. The ophthalmologist repeats the biostimulative treatment in successive and slightly overlapping location in an arc around the entire 360° of the globe. The dosimetry control system 55 typically includes microprocessor 65 together with appropriate software programs 66 and may be designed to modulate the power level of the laser source 25 at any level among a continuous range of power levels as the emitters project beams 35A–35n. The software 66 that is part of the dosimetry control system, as the term is used herein, includes a conventional software program, a program within a programmable chip, or any other form of algorithm carried in any form of memory storage system. Within the hardware portion of dosimetry control system 55, there may be a keyboard, disk drive or other non-volatile memory system, displays as are well known in the art for operating such a system (see FIG. 5).

The dosimetry control system can operate in a "basic" mode of operation, which means that the physician utilizes a pre-selected program to control to (i) the particular power level of laser source 25; (ii) the particular exposure duration of beams 35A–35n. The power level may range from about 1 mJ to 100 mJ for the above-described beam diameters, with a CW source or a rapidly pulsed source with pulse length ranging from 1–1000 ms. As described above, the total duration of treatment may range from about 1 second to 120 seconds.

Another operational mode, and a preferred mode, relates to use of a feedback-controlled mode based on signals from thermal sensor(s) 57 shown in FIGS. 6 & 8. In a first feedback-controlled mode, surface temperature at the anterior scleral surface 48 may be monitored by sensor array 57, such that dosimetry control system 55 may simply terminate laser energy delivery upon a detected surface temperature reaching a pre-set, for example any temperature in preselected from a range of about 42° C. to 55° C., each such temperature also optionally including a pre-selectable time period ranging from about 1 ms to 30 seconds. Thus, the detected temperatures at the anterior surface 48 of the sclera can be modeled (e.g., using Monte Carlo modeling as is known in the art) to predict the temperature in the region of the meshwork M for creating the biostimulation temperature parameters described above. In another feedback controlled-operational mode, the dosimetry control system 55 can be programmed to modulate power to one or more emitter locations based on feedback from the sensor array 50.

In yet another operational mode of the invention, herein called the time-sequenced (or gated) operational mode, the dosimetry control system 55 and more specifically the beam sequence controller 59 which is adapted to sequentially deliver laser energy at any given power level between the individual emitter locations 31A–31n. Such "sequential" delivery can provide energy delivery to only one particular spot in the meshwork M at a time, or any spot substantially remote from an adjacent spot (either in distance or time of delivery) to allow the thermal relaxation time relative to a particular to spot to diffuse the temperature within the absorbing medium. For example, the beam sequence controller 59 may randomly, or in a pre-set sequence, select only one single emitter to emit a beam at any moment in time thus sequencing between any adjacent or non-adjacent emitters;

or controller 59 may select from 2 to n non-adjacent emitters to emit beam simultaneously while sequencing between or among another single emitter or any combination of emitters 31a–31n. By this beam delivery sequencing means, and thermal modeling as is known in the art such as Monte Carlo modeling, beam sequencing patterns can be developed as a function of both the thermal relaxation time about a beam's propagation and the heat aborption characteristics of working face 30 to optimize the biostimulative temperature elevation in the trabecular meshwork.

Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A system for causing controlled thermal damage within a patient's trabecular meshwork to treat glaucoma, comprising:

a probe defining a distal face for contacting the surface of a patient's eye;

the distal face defining a surface area of at least 20 mm.$^2$ for acting as a heat sink;

at least one laser emitter carried in the distal face that delivers a wavelength from a laser source ranging between about 1.30–1.40 $\mu$m or 1.55–1.85 $\mu$m; and said emitter defining an emission axis aligned with the trabecular meshwork when the working surface is in contact with the patient's eye.

2. The system of claim 1 wherein the distal face for contacting the patient's eye has a surface area of about 40 mm.$^2$ or greater.

3. The system of claim 1 wherein the distal face for contacting the patient's eye has a surface area of about 60 mm.$^2$ or greater.

4. The system of claim 1 further comprising:

a temperature sensor carried in said distal face for generating a signal corresponding to the surface temperature of the patients' eye; and a controller for receiving and processing said signal to modulate power delivery by the said laser emitter.

5. The system of claim 1 wherein the distal face is impressed with intersecting first and second spherical receiving forms, said first form dimensioned to receive a portion of the patient's cornea, said second form dimensioned to receive a portion of the patient's sclera.

6. The system of claim 5 wherein the first spherical form defines a radius ranging between about 6.4 mm and 7.8 mm and the second spherical form defines a radius ranging between about 8.0 mm and 12.0 mm.

7. The system of claim 5 wherein said at least one laser emitter is carried in the second spherical form.

8. A system for creating a selected thermal effect within a patient's trabecular meshwork comprising:

a handpiece having a distal working face for contacting a portion of the sclera of said eye;

the working face defining a surface area of at least 20 mm.$^2$ for acting as a heat sink, a plurality of light emitters carried about a radial arc within said working face, said plurality of emitters adapted to irradiate a part-annular portion of said sclera and the underlying trabecular meshwork;

the emitters defining an emission axis aligned with the trabecular meshwork, and a laser source coupled to said plurality of emitters producing a wavelength ranging between 1.30–1.40 $\mu$m or 1.55–1.85 $\mu$m.

9. The system of claim 8 wherein said radial are of said plurality of emitters extends extends between 10° and 180° about said working face.

10. The system of claim 8 wherein each said plurality of emitters includes a lens element for focusing said light energy beam in a range of 750 $\mu$m to 900 $\mu$m beyond said lens element.

\* \* \* \* \*